(12) United States Patent
Wong

(10) Patent No.: US 11,280,863 B2
(45) Date of Patent: Mar. 22, 2022

(54) COILED ANTENNA WITH FLUID COOLING

(71) Applicant: INTUITIVE SURGICAL OPERATIONS, INC., Sunnyvale, CA (US)

(72) Inventor: Serena H. Wong, Los Altos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 134 days.

(21) Appl. No.: 16/670,947

(22) Filed: Oct. 31, 2019

(65) Prior Publication Data

US 2020/0142013 A1 May 7, 2020

Related U.S. Application Data

(60) Provisional application No. 62/858,719, filed on Jun. 7, 2019, provisional application No. 62/754,976, filed on Nov. 2, 2018.

(51) Int. Cl.
*H01F 27/28* (2006.01)
*A61B 18/18* (2006.01)
(Continued)

(52) U.S. Cl.
CPC ...... *G01R 33/3856* (2013.01); *A61B 18/1815* (2013.01); *G01R 33/34023* (2013.01);
(Continued)

(58) Field of Classification Search
CPC .......... G01R 33/3856; G01R 33/34023; G01R 33/3804; H01F 27/2876; H01F 6/06; H01F 5/00; H02J 3/008; A61B 2034/2059; A61B 2090/3614; A61B 34/37; A61B 2090/371; A61B 2034/2051; A61B 2034/2061; A61B 34/20; A61B 2018/00208; A61B 18/24; A61B 2018/00809; A61B 2018/00785; A61B 2018/00791; A61B 2018/00779;
(Continued)

(56) References Cited

U.S. PATENT DOCUMENTS 6,380,732 B1 4/2002 Gilboa
6,389,187 B1 5/2002 Greenaway et al.
(Continued)

OTHER PUBLICATIONS

C. Rappaport, "Treating cardiac disease with catheter-based tissue heating," in IEEE Microwave Magazine, vol. 3, No. 1, pp. 57-64, Mar. 2002 (Year: 2002).*
(Continued)

*Primary Examiner* — Daniel R Miller
(74) *Attorney, Agent, or Firm* — Haynes and Boone, LLP

(57) ABSTRACT

An energy delivery system comprises a transmission member and an antenna at a distal end of the transmission member. The antenna includes a first conductive arm, an insulator extending around the first conductive arm, and a second conductive arm. The second conductive arm includes a coil. The system also comprises a barrier layer radially spaced from the insulator and surrounding the transmission member and antenna. The barrier layer extends from a proximal portion of the transmission member to a distal portion of the antenna. The system also comprises a jacket surrounding the barrier layer and forming a fluid channel for flow of a cooling fluid.

20 Claims, 13 Drawing Sheets

(51) Int. Cl.
*H01F 5/00* (2006.01)
*A61B 18/00* (2006.01)
*G01R 33/385* (2006.01)
*G01R 33/34* (2006.01)
*H01F 6/06* (2006.01)
*H02J 3/00* (2006.01)

(52) U.S. Cl.
CPC ............. *H01F 5/00* (2013.01); *H01F 6/06* (2013.01); *H01F 27/2876* (2013.01); *A61B 2018/00023* (2013.01); *A61B 2018/00077* (2013.01); *A61B 2018/00083* (2013.01); *A61B 2018/00577* (2013.01); *A61B 2018/00714* (2013.01); *A61B 2018/00744* (2013.01); *A61B 2018/1838* (2013.01); *A61B 2018/1846* (2013.01); *A61B 2018/1892* (2013.01); *H02J 3/008* (2013.01)

(58) Field of Classification Search
CPC ........... A61B 2018/00875; A61B 2018/00845; A61B 2018/00827; A61B 2018/00886; A61B 2018/0066; A61B 2018/00714; A61B 2018/00744; A61B 2018/00642; A61B 2018/00166; A61B 2018/00285; A61B 2018/00029; A61B 2018/1869; A61B 2018/1876; A61B 2018/1838; A61B 2018/00559; A61B 2018/00446; A61B 2018/00351; A61B 2018/00404; A61B 2018/00494; A61B 2018/00511; A61B 2018/00517; A61B 2018/00529; A61B 2018/00541; A61B 2018/1846; A61B 2018/00982; A61B 2017/00323; A61B 2018/00011; A61B 2018/00023; A61B 2018/00101; A61B 18/1815; A61B 2018/00577; A61B 2018/1861
See application file for complete search history.

(56) References Cited

U.S. PATENT DOCUMENTS

| | | | |
|---|---|---|---|
| 7,416,681 | B2 | 8/2008 | Kim et al. |
| 7,772,541 | B2 | 8/2010 | Froggatt et al. |
| 7,875,024 | B2* | 1/2011 | Turovskiy ............. A61N 5/045 606/33 |
| 8,900,131 | B2 | 12/2014 | Chopra et al. |
| 9,259,274 | B2 | 2/2016 | Prisco |
| 9,452,276 | B2 | 9/2016 | Duindam et al. |
| 2008/0266203 | A1* | 10/2008 | Rossetto ............ A61B 18/1815 343/895 |
| 2009/0138005 | A1* | 5/2009 | Prakash ............ A61B 18/1815 606/33 |
| 2011/0213351 | A1* | 9/2011 | Lee .................... A61B 18/1815 606/33 |
| 2015/0119870 | A1* | 4/2015 | Rudie ................ A61B 18/1815 606/33 |
| 2018/0206902 | A1 | 7/2018 | Eggers et al. |
| 2021/0153936 | A1* | 5/2021 | Mosesov ............ A61B 18/1815 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

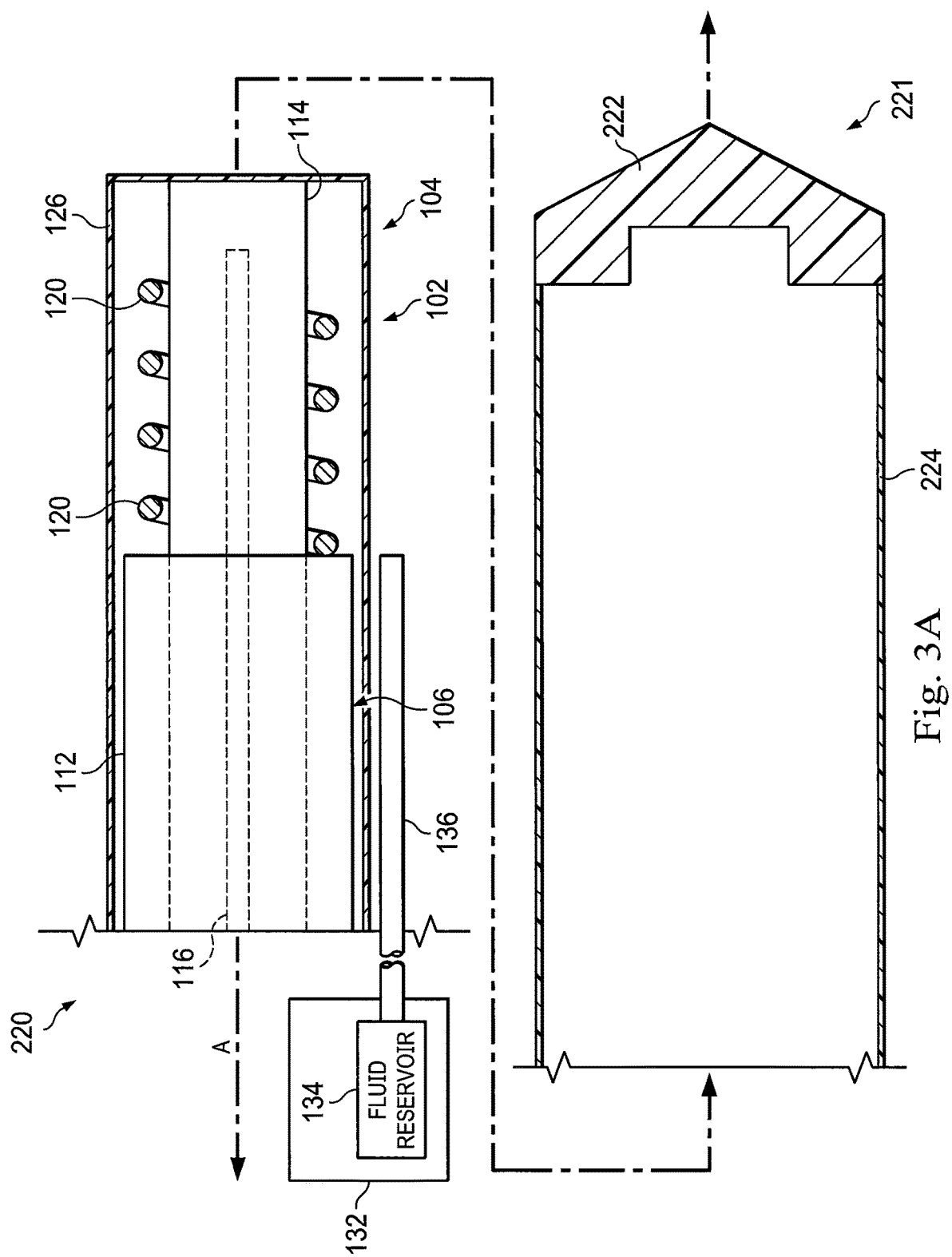

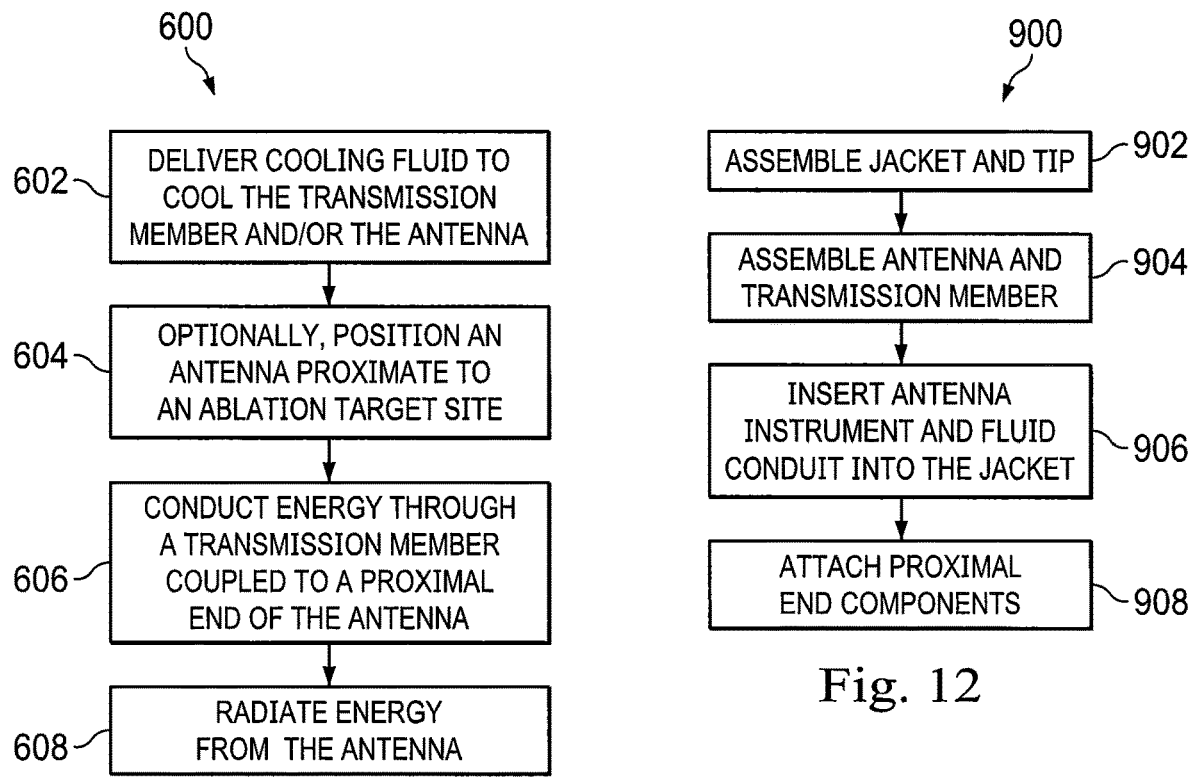
Fig. 9
Fig. 12
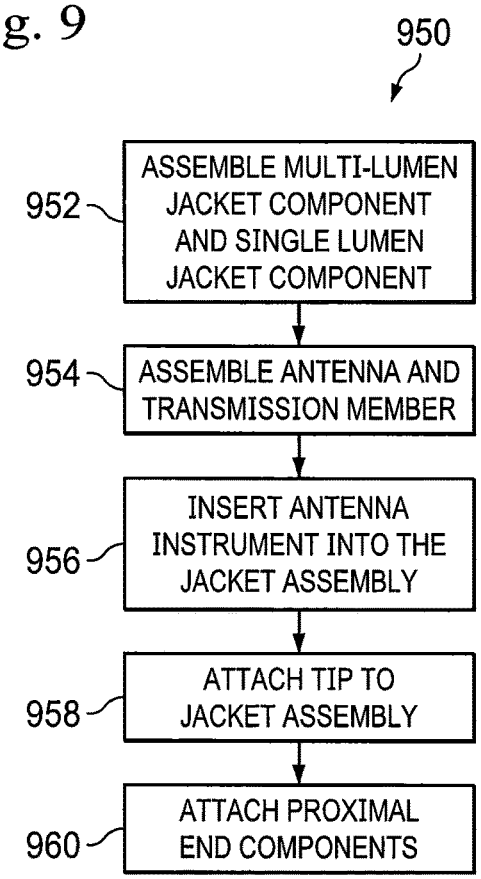
Fig. 13

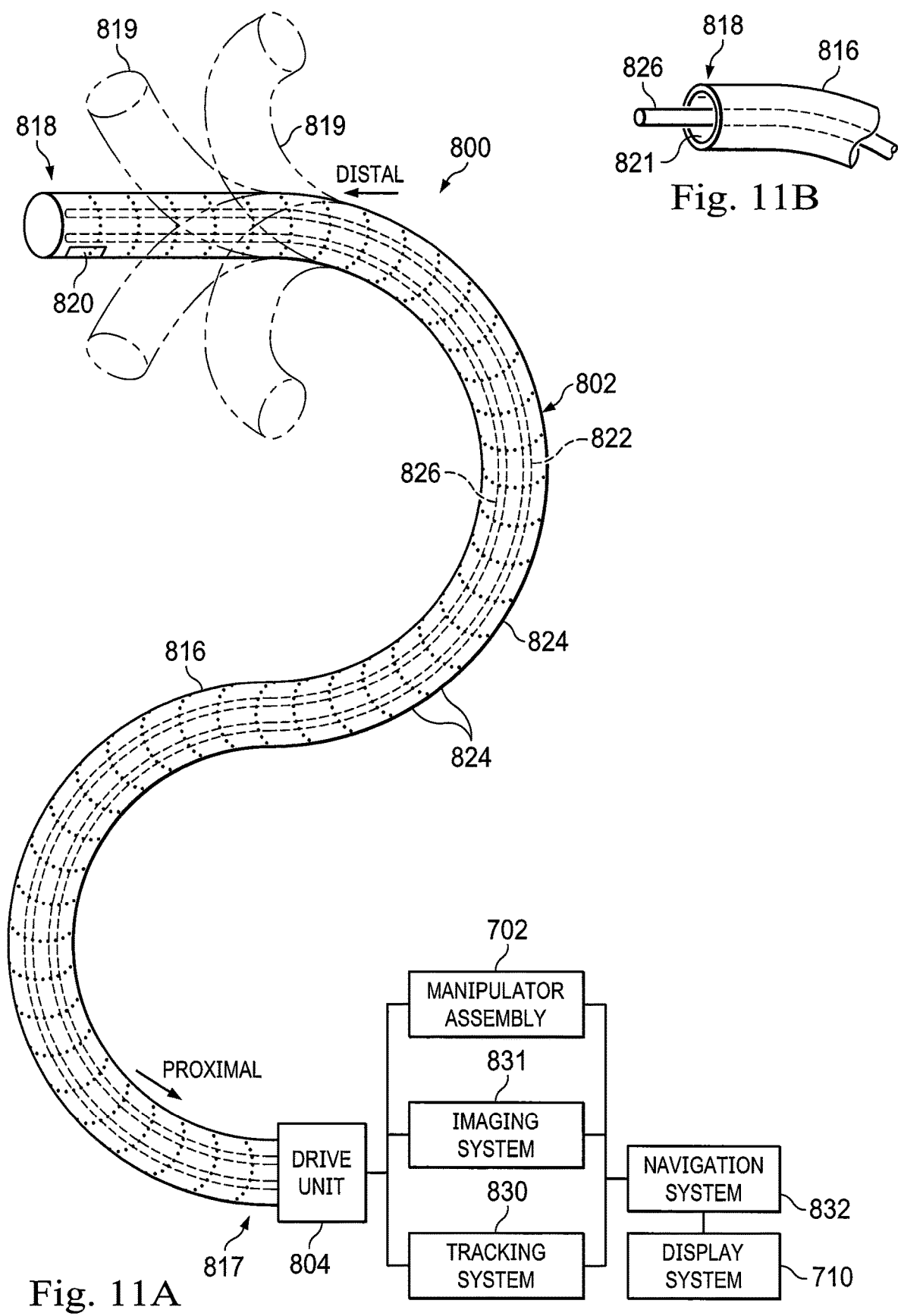

COILED ANTENNA WITH FLUID COOLING

CROSS-REFERENCE TO RELATED APPLICATIONS

This application claims the benefit of U.S. Provisional Application 62/754,976 filed Nov. 2, 2018 and U.S. Provisional Application 62/858,719 filed Jun. 7, 2019, all of which are incorporated by reference herein in their entirety.

FIELD

The present disclosure is directed to minimally invasive ablation systems and methods of use.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Minimally invasive medical tools may also include ablation instruments. Ablation instruments transmit energy in the form of electromagnetic waves to a targeted area of tissue, such as a tumor or other growth, within the patient anatomy to destroy the targeted tissue. Some minimally invasive medical tools and ablation instruments may be teleoperated or otherwise computer-assisted. Various features may improve the effectiveness of minimally invasive ablation instruments.

SUMMARY

Embodiments of the invention are best summarized by the claims that follow the description.

In some examples, an energy delivery system comprises a transmission member and an antenna at a distal end of the transmission member. The antenna includes a first conductive arm, an insulator extending around the first conductive arm, and a second conductive arm. The second conductive arm includes a coil. The system also comprises a barrier layer surrounding the transmission member and antenna. The barrier layer extends from a proximal portion of the transmission member to a distal portion of the antenna. The system also comprises a jacket surrounding the barrier layer and forming a fluid channel for receipt of a cooling fluid.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 3A is an exploded cross-sectional side view of an energy delivery system according to some embodiments.

FIG. 9 is a flowchart illustrating a method of ablation according to some embodiments.

FIG. 11A is a simplified diagram of a medical instrument system according to some embodiments.

FIG. 11B is a simplified diagram of a medical instrument with an extended medical tool according to some embodiments.

FIG. 12 illustrates a method for manufacturing an energy delivery system.

FIG. 13 illustrates a method for manufacturing an energy delivery system.

Figure 1:
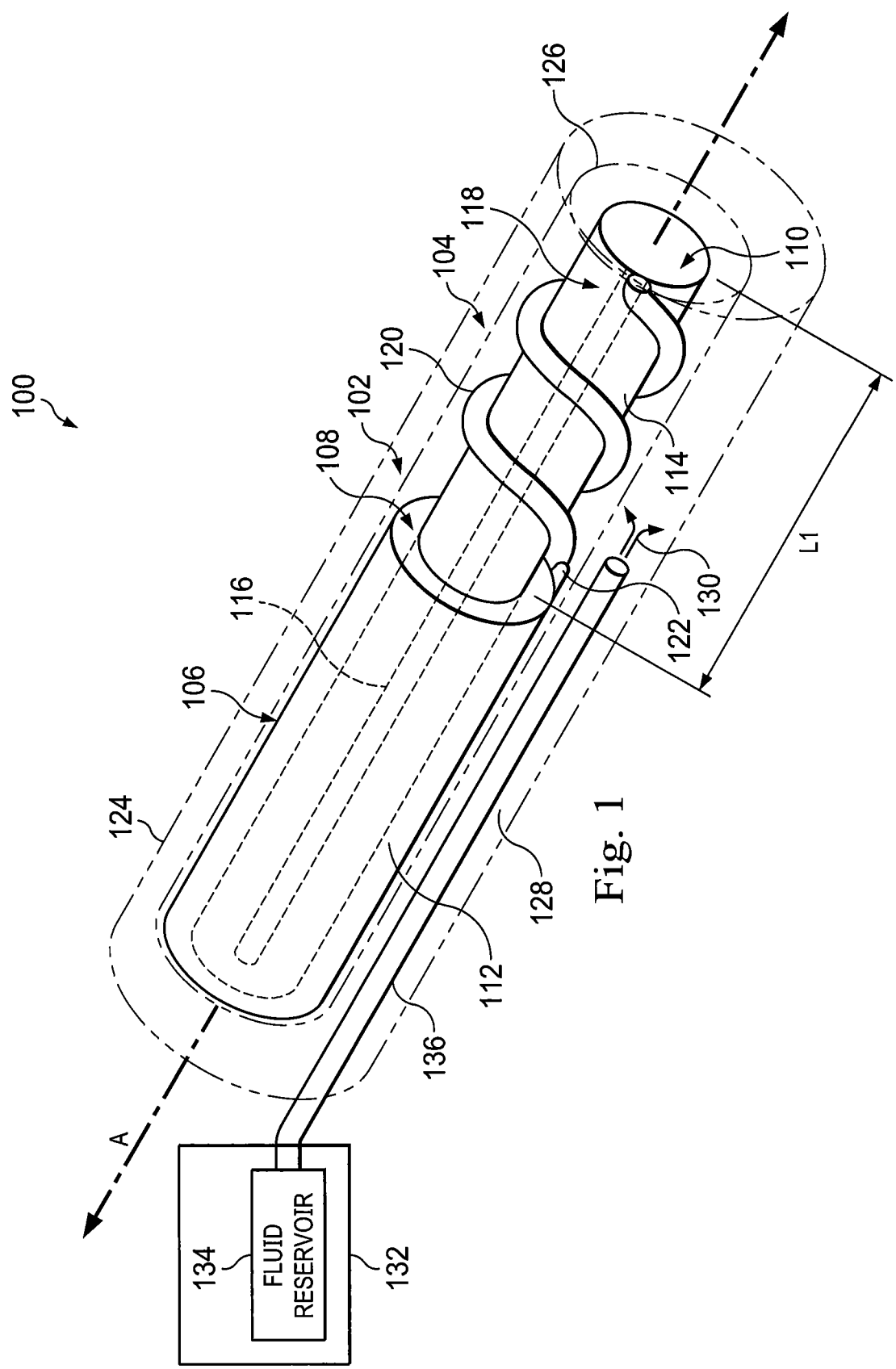
FIG. 1 is a perspective view of an energy delivery system for tissue ablation with an antenna coupled to a transmission member according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIGS. 1-8 illustrate various embodiments of energy delivery systems. In some embodiments, the energy delivery systems are used for tissue ablation, causing an increase in a temperature of an anatomic target area by transmitting electromagnetic waves from the energy delivery system to the anatomic target area, or ablation site. To prevent excessive heating that may cause unwanted damage to patient tissue, the energy delivery system may be cooled by fluid as disclosed in the following embodiments. In some embodiments, the energy delivery systems may be flexible and suitable for use in, for example, surgical, diagnostic, therapeutic, ablative, and/or biopsy procedures. In some embodiments, the energy delivery systems may be used as a medical instrument in an image-guided medical procedure performed with a teleoperated medical system as described in further detail below. While some embodiments are provided herein with respect to such procedures, any reference to medical or surgical instruments and medical or surgical methods is non-limiting. In some embodiments, the energy delivery systems may be used for non-teleoperational or non-robotic procedures involving traditional manually operated medical instruments. The systems, instruments, and methods described herein may be used for animals, human cadavers, animal cadavers, portions of human or animal anatomy, non-surgical diagnosis, as well as for industrial systems and general robotic, general teleoperational, or robotic medical systems.

As shown in FIG. 1, an energy delivery system 100 generally includes a flexible antenna instrument 102 which includes an antenna 104 extending from an elongate transmission member 106. The antenna 104 extends between a proximal end 108 and a distal end 110. The elongate transmission member 106 includes an outer conductor 112 at least partially surrounding an inner conductor 116 and includes an insulator 114 (e.g., a dielectric layer) substantially surrounding the inner conductor 116, insulating the outer conductor 112 from the inner conductor 116. In this embodiment, the insulator 114 and the inner conductor 116 extend distally beyond the outer conductor 112. In this embodiment, elongate transmission member 106 is a coaxial cable but for simplicity, jacket layers and other details may not be illustrated. Other coaxial cable configurations with different configurations, shapes, etc. of inner conductor, outer conductor, and dielectric layers could also be used. In alternative embodiments, any type of elongate transmission member may be used for the antenna instrument 102.

In this embodiment, antenna 104 is a helical dipole antenna extending along a longitudinal axis A and may be used to radiate microwave energy for use in the tissue ablation process. More specifically, antenna 104 is used to create electromagnetic radiation within a wavelength range of one meter to one millimeter, and within a frequency range of approximately 300 Megahertz (MHz) TO 300 Gigahertz (GHz) (e.g., a microwave). A microwave, which is a type of radio wave, is made up of a magnetic field at a right angle to an electric field, and both the magnetic field and the electric field oscillate at a specific frequency and travel together along a direction that is perpendicular to both the magnetic field and the electric field. In some embodiments, the wavelength and the frequency of the microwaves being radiated by antenna 104 may be modified to cause a desired type of ablation at the ablation target site.

In this embodiment, the dipole antenna 104 includes a portion 118 of inner conductor 116 distal of the outer conductor 112 as a first arm of the dipole antenna 104. A conductive coil 120 is wound around the insulator 114 surrounding the portion 118 of inner conductor 116. The coil 120, which may be a helically shaped coil, forms a second arm of the dipole antenna 104. The coil 120 may be looped around an outer perimeter of the exposed portion of insulator 114 a plurality of times to form a spiral-shape. The insulator 114 may insulate the outer conductor 112 from the inner conductor 116 and also insulate the inner conductor 116 from the coil 120. The coil 120 may be electrically coupled (e.g., soldered) to outer conductor 112 by an electrical coupling 122.

In some embodiments, the material of the insulator 114 may be chosen to provide a high axial stiffness along axis A to allow greater rigidity to puncture tissue. Rigid materials such as polyetheretherketone (PEEK) or polyetherimide (e.g. Ultem) may be used, for example, to increase stiffness in the antenna and prevent buckling during a puncture operation.

In some embodiments, the coil 120 may extend along the entire length L1 of portion 118 of the inner conductor 116 or along a substantial portion of length L1 (e.g. from 90% to 100%) to allow bending stiffness and mechanical properties of the entire antenna 104 to be uniform, particularly under bending when the antenna forms a constant curvature. In some embodiments, the coil 120 may extend only partially along the length L1 of portion 118 of the inner conductor. In some other embodiments, the coil 120 may be a double-helix coil extending along opposing sides of inner conductor 116 and insulator 114. In some other embodiments, coil 120 may wrap back over itself in an overlapped coil shape. In some embodiments, coil 120 may include two tubes wound together to create a helically wound double coil. In some embodiments, coil 120 may extend only partially along the exposed surface of the inner conductor. In alternative embodiments, coil 120 may be configured in any way that facilitates operation of antenna instrument 102 as described herein.

A barrier layer 126 extends along the antenna instrument 102, creating a barrier or seal to prevent inward migration of fluid. The barrier layer 126 may be formed of a thermoplastic such as polyethylene terephthalate (PET) or other flexible and fluid insulating and impermeable materials. The barrier layer 126 may be thin and form fit around the components of the antenna instrument 102 or may maintain a flexible tubular form. In some embodiments, the barrier layer may provide added rigidity to support the antenna 104.

The antenna instrument 102 is disposed within a jacket 124. In some embodiments the jacket 124 is closed, sealed, or otherwise restricts fluid from passing into or out of the jacket. In alternative embodiments, jacket 124 may have openings, slits, or otherwise be unsealed along any portion of jacket 124 to allow fluid to pass into the jacket or out from the jacket. The jacket may be formed from a thermoplastic or other flexible and fluid impermeable materials.

A channel 128 is formed between the jacket 124 and the barrier layer 126 and receives a fluid 130 to cool the antenna instrument 102. The fluid 130 may be, for example, water or a saline solution. The fluid 130 may be provided to the channel 128 from a fluid cooling system 132 that is coupled to the channel 128. The fluid cooling system 132 may include a fluid reservoir 134 and other components such as pumps, valves, refrigeration systems, suction systems, sensors (not shown). The fluid cooling system 132 can also include or be coupled to a fluid conduit 136 that extends through the channel 128. The fluid 130 may be directed within the channel 128 through the conduit 136. In alternative embodiments, the conduit 136 may be omitted with the fluid delivered directly through the channel 128 such that it contacts an inner wall of the channel 128. In some embodiments the fluid cooling system 132 may be an open loop system, a partially open loop system, a closed loop system or any other suitable type of cooling system. As described below, a plurality of conduits may be used, with at least one conduit providing inflow of the fluid 130 to the channel 128 (for a partially open loop or closed loop system) and at least one conduit providing a return flow to remove fluid 130 from the channel 128.

The conduit 136 may include tubing made of braided tubing or nitinol tubing that provides mechanical properties needed for spring back and stiffness (to reduce trajectory error). If constructed from nitinol, the tubing can be laser cut or ground to adjust stiffness over the length of the channel. This can provide for a gradual transition and eliminate kinking near the antenna body. In some embodiments, nitinol is required only near a distal end portion of the channel so, to reduce costs, a proximal length of the channel can be made of polyimide or plastic and a distal end portion can be nitinol glued to the proximal length. In some embodiments, a fluorinated ethylene propylene (FEP) layer may surround the conduit 136. A minimum wall thickness of the conduit 136 may be necessary to prevent kinking of the channel. The wall thickness may, however, limit the overall cross sectional area of other components within the device in order to maintain a desired total outer diameter.

In alternative embodiments, the structure of the coil 120 may be selected to mitigate overheating of the coil. For example, an antenna formed from a large diameter wire forming the coil paired with a large diameter inner conductor may generate less heat than an antenna formed from a small diameter wire forming the coil paired with a small diameter inner conductor. However, the thicker coil wire may reduce the antenna flexibility and increase the antenna's likelihood of deformation. Thus, in some embodiments, a wire diameter may be chosen to provide for a desired device flexibility while minimizing heat generation.

Figure 2A:
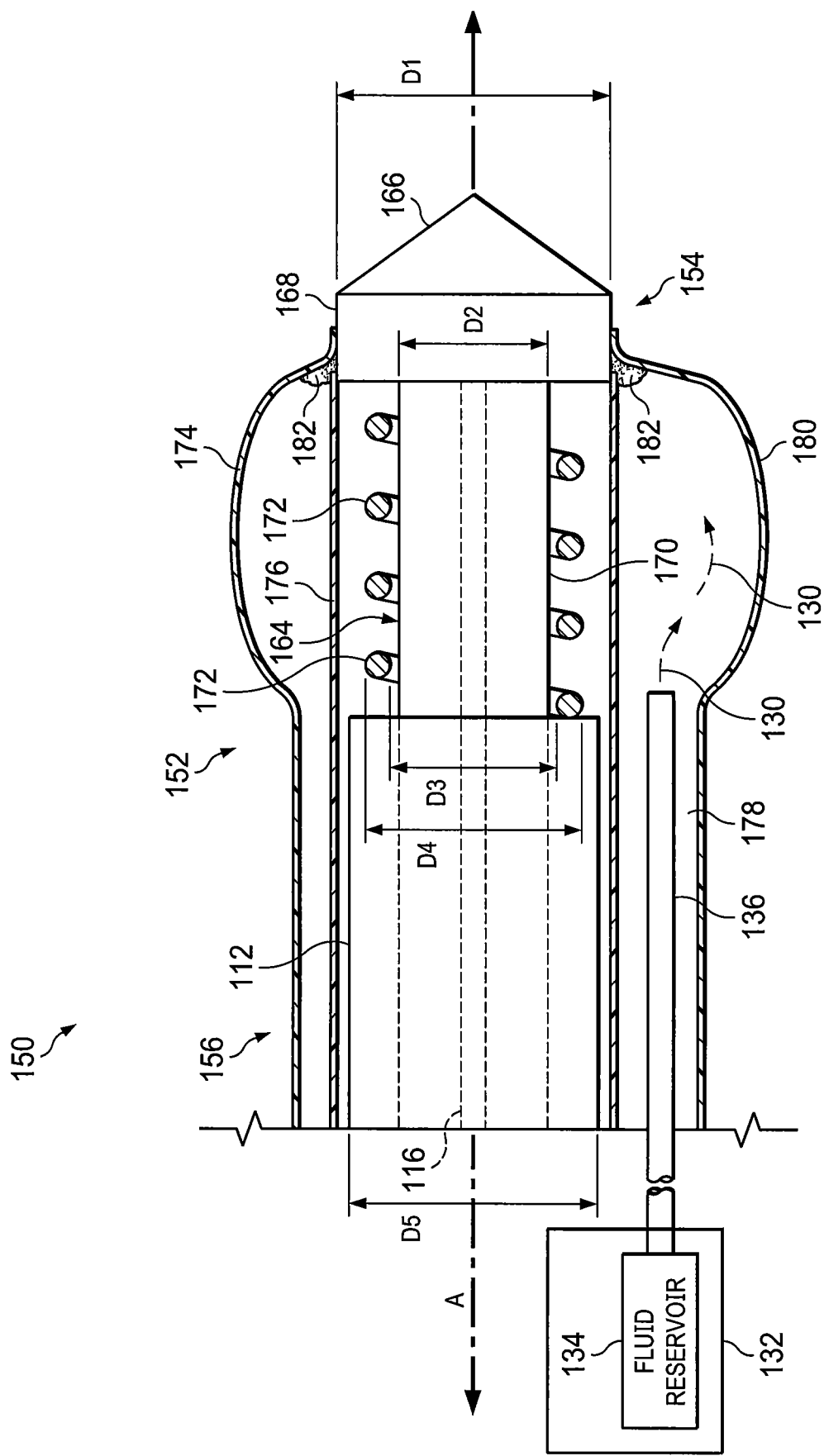
FIG. 2A is a cross-sectional side view of an energy delivery system with a fluid cooling system and a jacket including a balloon portion.

FIG. 2A is a cross-sectional side view of an energy delivery system 150. The energy delivery system 150 generally includes a flexible antenna instrument 152 which includes a dipole antenna 154 extending from an elongate transmission member 156. The elongate transmission member 156 includes the outer conductor 112 at least partially surrounding the inner conductor 116 and includes an insulator 164 (e.g. a dielectric layer) substantially surrounding the inner conductor 116, insulating the outer conductor 112 from the inner conductor 116. The outer conductor 112 and inner conductor 116, may be substantially similar to the previously described structures with the same reference numerals. In this embodiment, the insulator 164 includes a pointed tip 166, a section 168 having a width (e.g. a diameter) D1, and a section 170 having a width (e.g., a diameter) D2. In this embodiment, D1 is larger than D2 which may help in construction of the pointed tip 166 by providing more material to form the pointed tip 166 while still maintaining a smaller overall outer diameter for the antenna 154. The pointed tip 166 of the insulator 164 may allow the antenna instrument 152 to more easily puncture anatomic tissue. In some embodiments, the pointed tip 166 may be formed in any shape including any number of faces forming the tip, at any angle and/or with any ratio of sizes (e.g. width vs. length) that will Optimize tissue penetration. Various tips for optimizing tissue penetration are described in co-pending U.S. patent application Ser. No. 16/670,846, filed Oct. 31, 2019, disclosing "Tissue Penetrating Device Tips," which is incorporated by reference herein in its entirety.

A conductive coil 172 (which may be substantially similar to coil 120, with differences as described) is wrapped around the section 170 of the insulator 164 forming the second arm of the dipole antenna 154. The conductive coil 172 may be tightly coiled around the insulator 164 such that an inner diameter D3 of the coil 172 is approximately the same or just slightly larger than the outer diameter D2 of the insulator 164. In this embodiment, an outer diameter D4 of the coil 172 is approximately the same as or smaller than the outer diameter D5 of the transmission member 156, allowing for better fluid flow around the conductive coil 172 in some embodiments. In alternative embodiments, the coil 172 may be more loosely wound such that the outer diameter D4 of the coil 172 is larger than the outer diameter D5 of the transmission member.

The energy delivery system 150 includes a barrier layer 176 extending along the antenna instrument 152, creating a barrier or seal to prevent inward migration of fluid. The barrier layer 176 may be formed of a thermoplastic or other flexible and fluid impermeable materials. The barrier layer 176 may form fit around the components of the antenna instrument 102 or may maintain a flexible tubular form. In some embodiments, the barrier layer 176 may provide added rigidity to support the antenna 154. As shown in this embodiment, the barrier layer 176 may terminate at and be bonded to the insulator 164 at the section 168.

The energy delivery system 150 also includes a jacket 174 extending along the antenna instrument 152. A channel 178 is formed between the jacket 174 and the barrier layer 176. In this embodiment, the jacket 174 includes a balloon portion 180 adjacent to the antenna 154 that allows the channel 178 to expand to accommodate cooling fluid. A distal portion of the jacket 174 may be bonded to the insulator 164 and/or to the barrier layer 176 by a bonding material 182 to seal the jacket and prevent migration of fluid beyond the jacket.

The energy delivery system 150 also comprises the fluid cooling system 132, including the fluid reservoir 134 and may be coupled to or include the fluid conduit 136. In this embodiment, the fluid conduit 136 may terminate proximal to, at, or near the distal end of the outer conductor 112. In alternative embodiments, the fluid conduit 136 may extend distally of the outer conductor 112. As fluid 130 is directed into the channel 178, a cavity 184 formed by the barrier layer 176 and the balloon portion 180 of the jacket 174 may fill with the fluid 130. The fluid 130 in the cavity 184 may surround and cool the coil 172. In some embodiments, the fluid 130 may be evacuated from the channel 178 and the cavity 184 via a negative pressure that directs the fluid around the fluid conduit 136 in a direction opposite the direction of delivery flow through the conduit 136. In some embodiments, the fluid 130 may be evacuated from the channel 178 by a reverse flow through the fluid conduit 136. Various other embodiments for delivering and evacuating fluid are described below.

Figure 2B:
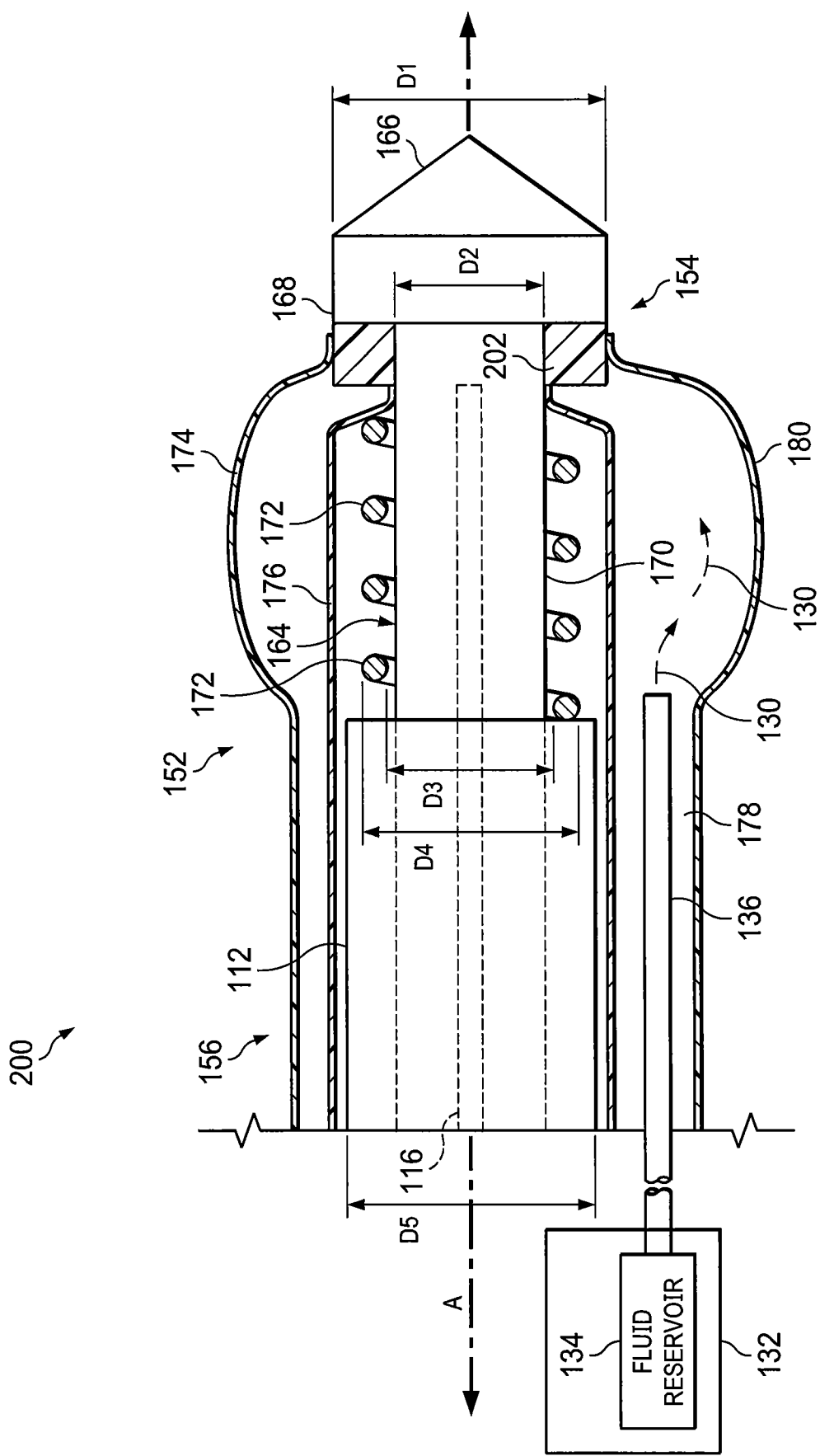
FIG. 2B is a cross-sectional side view of an energy delivery system with a fluid cooling system and a jacket including a balloon portion.

FIG. 2B is a cross-sectional side view of an energy delivery system 200. Energy delivery system 200 may be substantially similar to energy delivery system 150 with the differences as described. In this embodiment, a ring 202 may extend around the section 170 of insulator 164. A distal portion of the jacket 174 may be bonded to the ring 202 to form a seal that prevents migration of fluid beyond the jacket. In this embodiment, the barrier layer 176 may be bonded to the insulator 164. In some embodiments, the ring may be formed of a PEBAX nylon or other materials that bond with the jacket 174 to create a seal between the ring and the jacket.

Figure 3B:
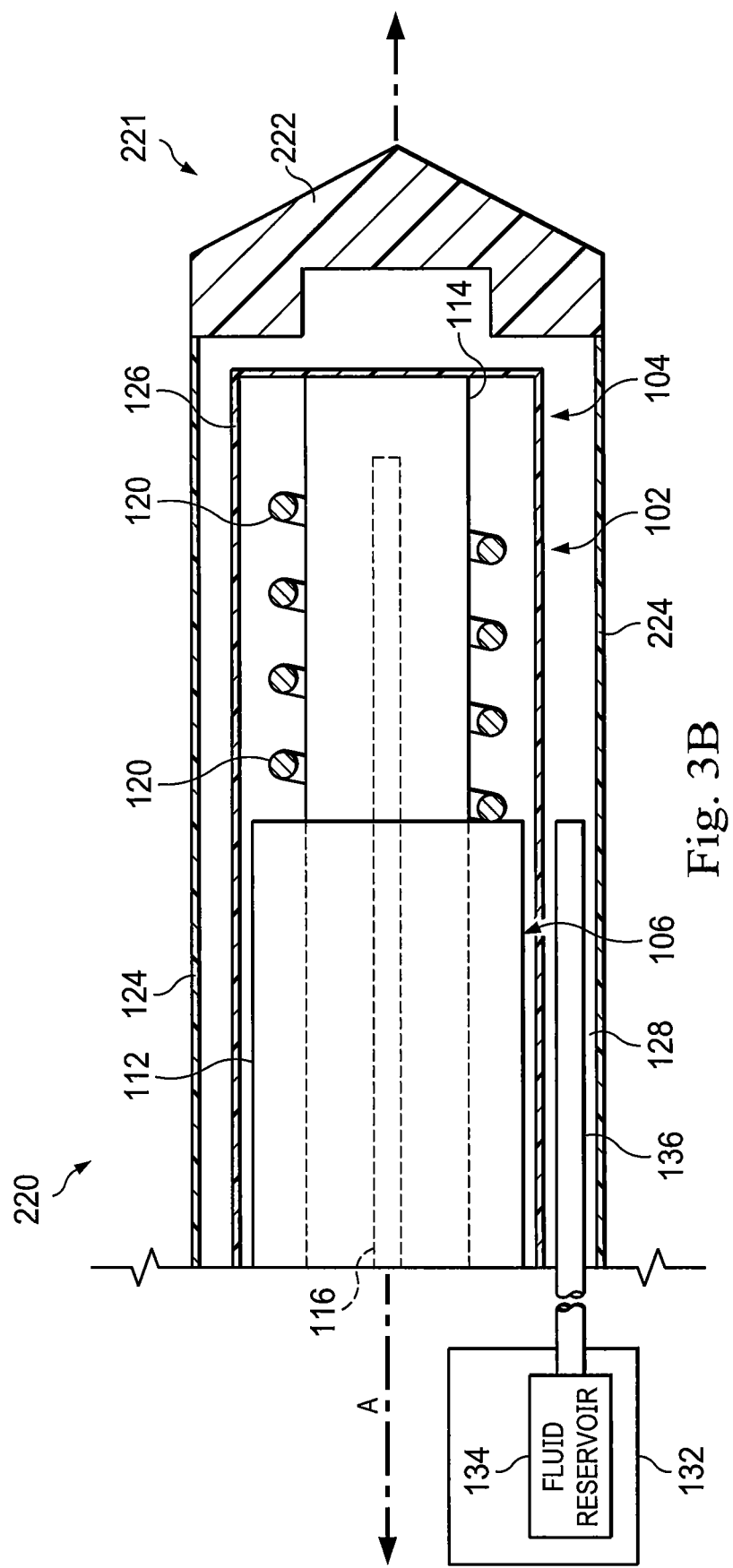
FIG. 3B is an assembled cross-sectional side view of the energy delivery system of FIG. 3A.
Figure 3C:
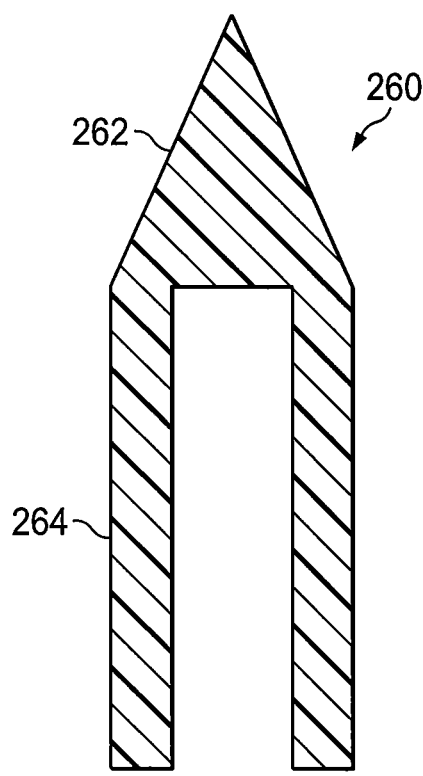
FIG. 3C illustrates a monolithic jacket and tip structure according to some embodiments.

FIG. 3A is an exploded cross-sectional side view of an energy delivery system 220. FIG. 3B is an assembled view of the energy delivery system 220. Energy delivery system 220 may be substantially similar to energy delivery system 100 with the differences as described. In this embodiment, an assembly 221 comprising an outer jacket 224 and a tip section 222 are assembled separately from the assembly of the antenna instrument 102. In some embodiments, the tip section could include a hollow area as shown so that the center of the antenna could nestle into the tip section, allowing the center conductor and the dielectric to provide better rigidity. In that embodiment, the antenna 114 (still surrounded by the barrier layer 126) may be shaped with a smaller diameter extension which would fit within the hollow. As shown in FIG. 3B, the antenna instrument 102 and the conduit 136 may be inserted into the assembly 221 and fitted together to form the energy delivery system 220. In this embodiment, the outer jacket 224 is coupled to and sealed with the tip section 222, such that fluid from the assembly 221 is prevented from migrating outside of the outer jacket 224. In alternative embodiments, jacket 224 may have openings, slits, or otherwise be unsealed along any portion of jacket 224 to allow fluid to pass into the jacket or out from the jacket. The jacket may be formed from a thermoplastic or other flexible and fluid impermeable materials. The tip section 222 is pointed and may be more rigid than the jacket 224. The tip section 222 be formed of the same material as or a material similar to the insulator 114. For example, the tip section 222 may be formed of a dielectric material. In one embodiment, as shown in FIG. 3C, a monolithic jacket and tip structure 260 may be formed such that the tip 262 may be formed from the same material as the jacket 264. To form this tip, a glass mold can be heated and used to melt the end of the jacket tube into the desired shape (conical, dome, etc.)

Figure 3D:
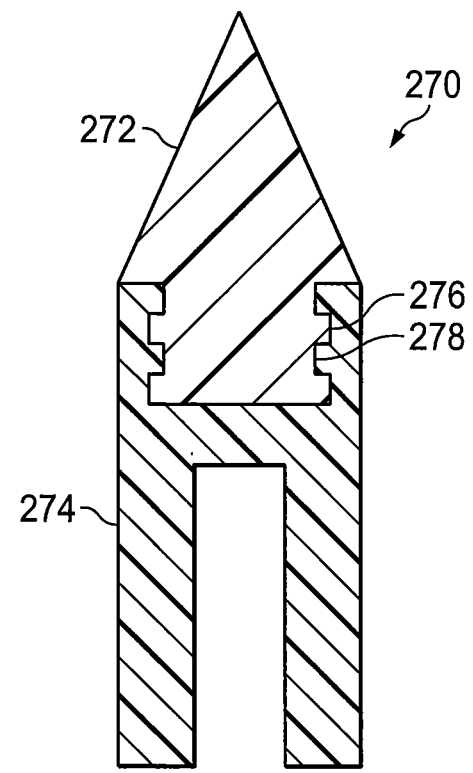
FIG. 3D illustrates a jacket and tip structure according to some embodiments.

In another embodiment, as shown in FIG. 3D, a jacket/tip structure 270 includes a tip 272 attached to a jacket 274. In this case, depending on the materials that are used, a glue joint or mechanical joint, for example can be used. In the case of a mechanical joint, ridges 276 and/or slots 278 or other types of grooves or attachment features can be machined into the side of the tip 272. The jacket 274 may be melted into and or onto these attachment features to form a mechanical bond. In some embodiments, the jacket may be constructed of a material which flows as it is melted, such as FEP. If an adhesive such as glue is used, the two materials may need to be prepared according to manufacturing instructions in order join the materials together.

In some embodiments, the antenna instrument 102 may be off-center or otherwise not coaxially with the assembly 221, providing a larger channel 128 for the conduit 136. The larger channel 128 may allow for a larger diameter conduit 136 or multiple conduits to provide sufficient fluid volume.

Figure 4A:
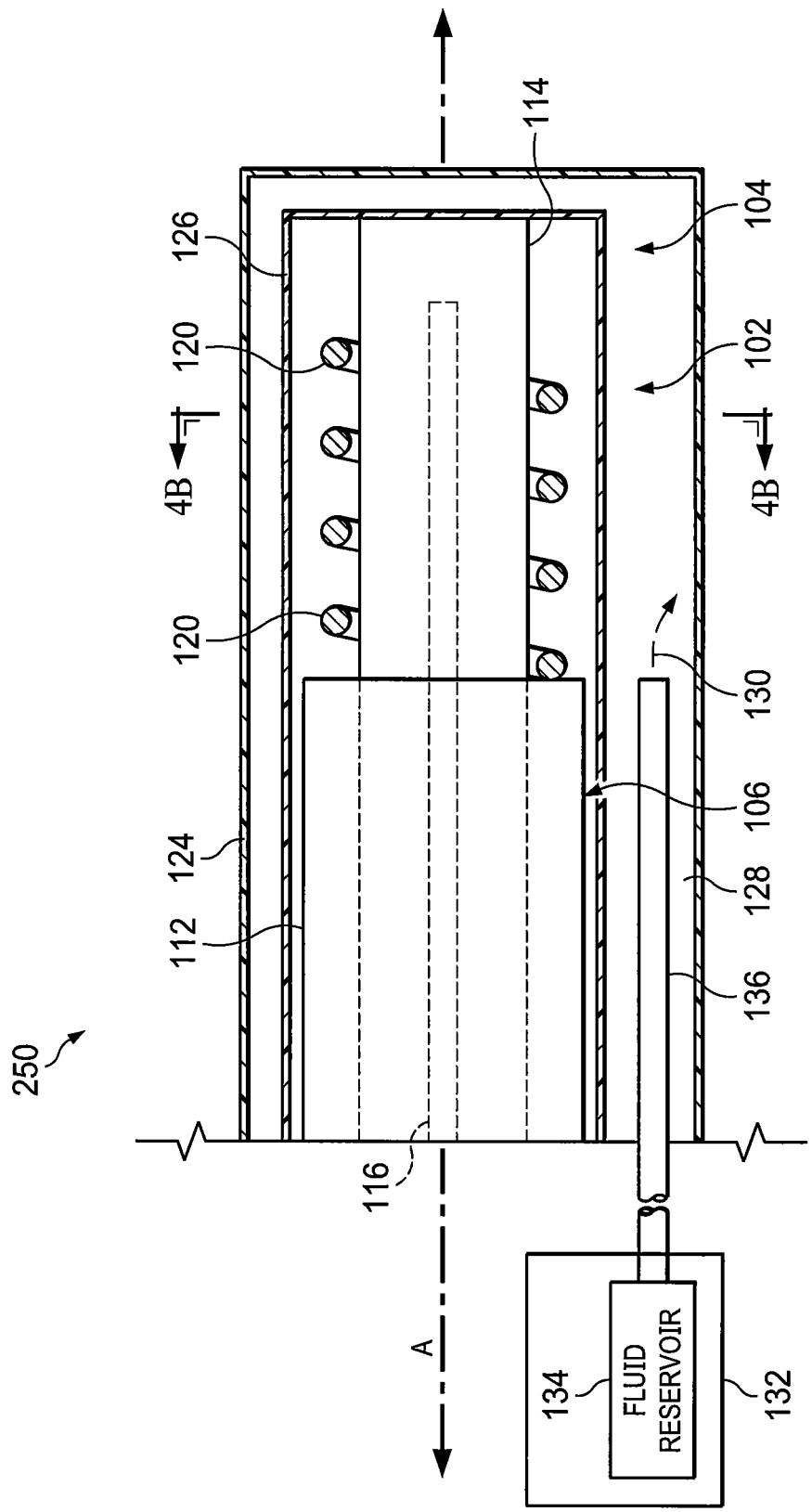
FIG. 4A is a cross-sectional side view of an energy delivery system with a fluid cooling system and a pair of fluid conduits.
Figure 4B:
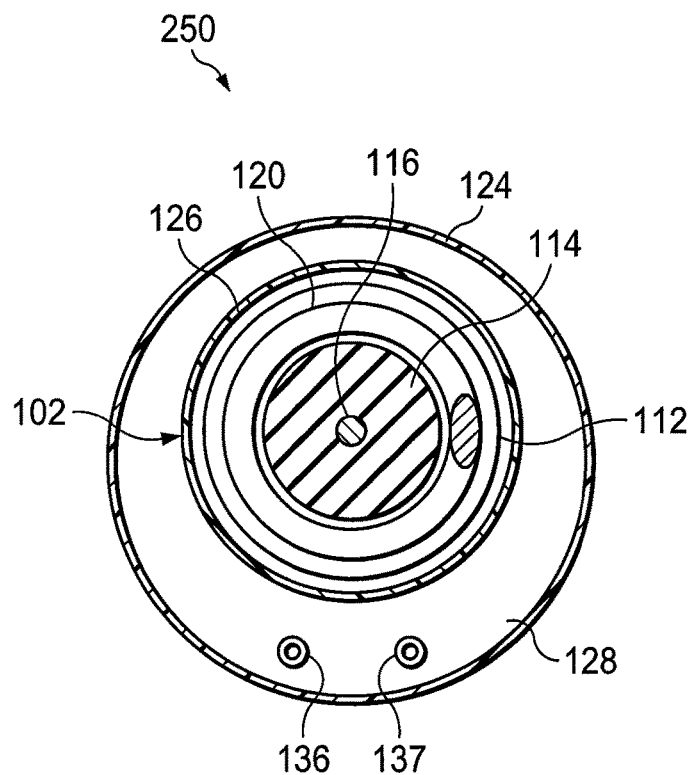
FIG. 4B is a cross-sectional end view of an energy delivery system of FIG. 4A with a fluid cooling system and a pair of fluid conduits.

FIGS. 4A and 4B are a cross-sectional side views and a cross-sectional end view, respectively, of an energy delivery system 250. Energy delivery system 200 may be substantially similar to energy delivery system 100 with the differences as described. In this embodiment, the fluid cooling system 132 includes or may be coupled to fluid conduit 136 aligned generally parallel with a conduit 137 (illustrated in FIG. 4B), both conduits extending with the channel 128. In one example, conduit 136 may supply fluid 130 along the elongate transmission member 106 and deliver the fluid to portion of the channel 128 surrounding the antenna 104. The conduit 137 may provide a suction force to evacuate the fluid 130 from the channel 128. In this embodiment, the flow of fluid 130 in the conduit 136 is opposite the flow of fluid in the conduit 137. In some embodiments, multiple conduits may be arranged radially around the antenna instrument 102, providing multiple routes for delivery and evacuation of fluid. In some embodiments, the delivery and evacuation conduits may be connected such that the fluid circulates entirely within the conduits without being released into the channel 128. In various embodiments, the conduits 136, 137 may terminate at any length along the antenna instrument 102.

Figure 5:
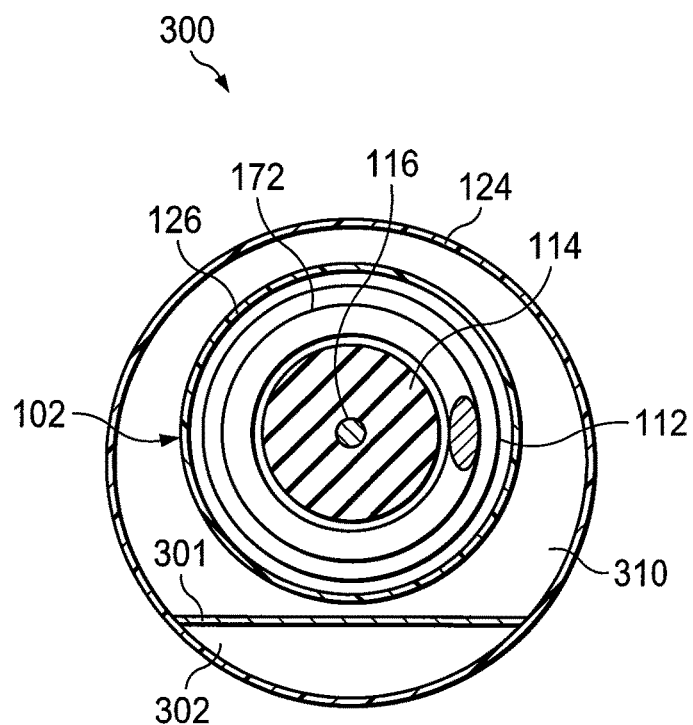
FIG. 5 is a cross-sectional end view of an energy delivery system with a D-shaped fluid channel.

FIG. 5 is a cross-sectional end view of an energy delivery system 300. Energy delivery system 300 may be substantially similar to energy delivery system 100 with the differences as described. In this embodiment, the fluid cooling system 132 includes a divider 301 which extends within channel 310 formed between jacket 124 and barrier layer 126. The divider 301 can extend along the length of the antenna instrument 102 and is connected between interior walls of the jacket 124. The divider 301 may terminate at any length along the antenna instrument 102. The jacket 124 and the divider 301 define a D-shaped channel 302 through which the fluid 130 may be delivered and evacuated.

Figure 6:
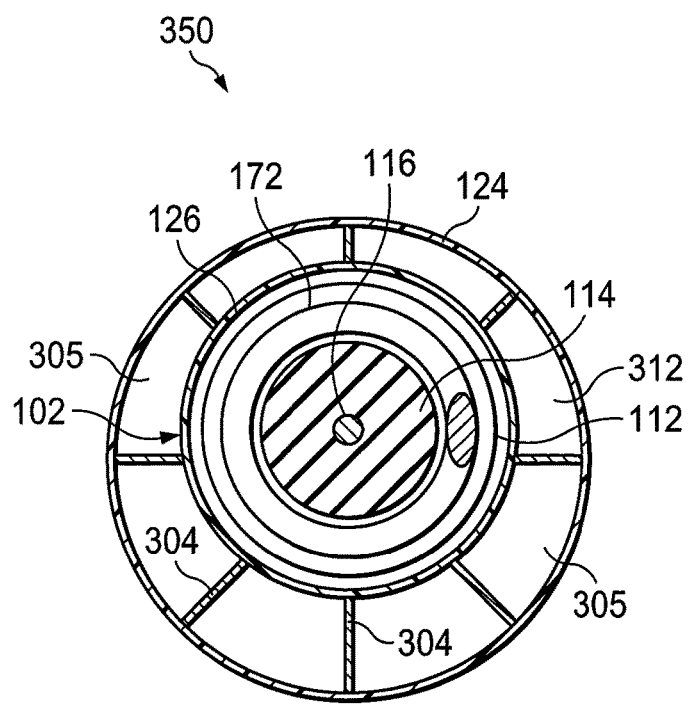
FIG. 6 is a cross-sectional end view of an energy delivery system with a plurality of dividers extending within a fluid channel to provide radially arranged inlet and outlet sub-channels within the fluid channel.

FIG. 6 is a cross-sectional end view of an energy delivery system 350. Energy delivery system 350 may be substantially similar to energy delivery system 100 with the differences as described. In this embodiment, the fluid cooling system 132 includes a plurality of dividers 304 which each extend within channel 312 formed between jacket and barrier layer 126. Each of the dividers 304 can extend within the channel 128 along the length of the antenna instrument 102. The dividers 304 are connected between the interior wall of the jacket 124 and the barrier layer 126. The dividers 304 may terminate at any length along the antenna instrument 102. The jacket 124, the barrier layer 126, and the dividers 304 define radially-arranged, arc-shaped sub-channels 305 through which the fluid 130 may be delivered and evacuated. For example, a plurality of the sub-channels 305 may be used for fluid delivery and a plurality of the sub-channels may be used for fluid evacuation. In some embodiments, one or more of the dividers 304 may terminate at a different lengths along the longitudinal axis of the antenna instrument 102 to, for example, accommodate the cooling of areas of uneven heating in the antenna.

Figure 7:
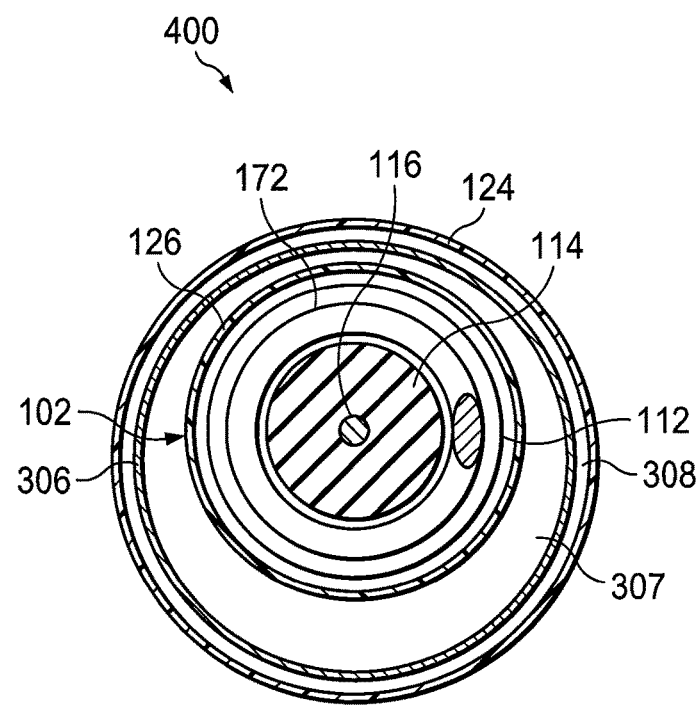
FIG. 7 is a cross-sectional end view of an energy delivery system with a divider extending with a fluid channel to provide concentric inlet and outlet sub-channels within the fluid channel.

FIG. 7 is a cross-sectional view of an energy delivery system 400. Energy delivery system 400 may be substantially similar to energy delivery system 100 with the differences as described. In this embodiment, the fluid cooling system 132 includes an elongate tubular divider 306 extending within the channel 128, along the length of the antenna instrument 102. In some embodiments, the divider 306 may be generally concentric with the antenna instrument 102. The divider 306 may terminate at any length along the antenna instrument 102. The jacket 124, the barrier layer 126, and the divider 306 define concentric ring-shaped sub-channels 307, 308 through which the fluid 130 may be delivered and evacuated. For example, an inner sub-channel 307 may be used for fluid delivery and an outer sub-channel 308 may be used for fluid evacuation.

Figure 8:
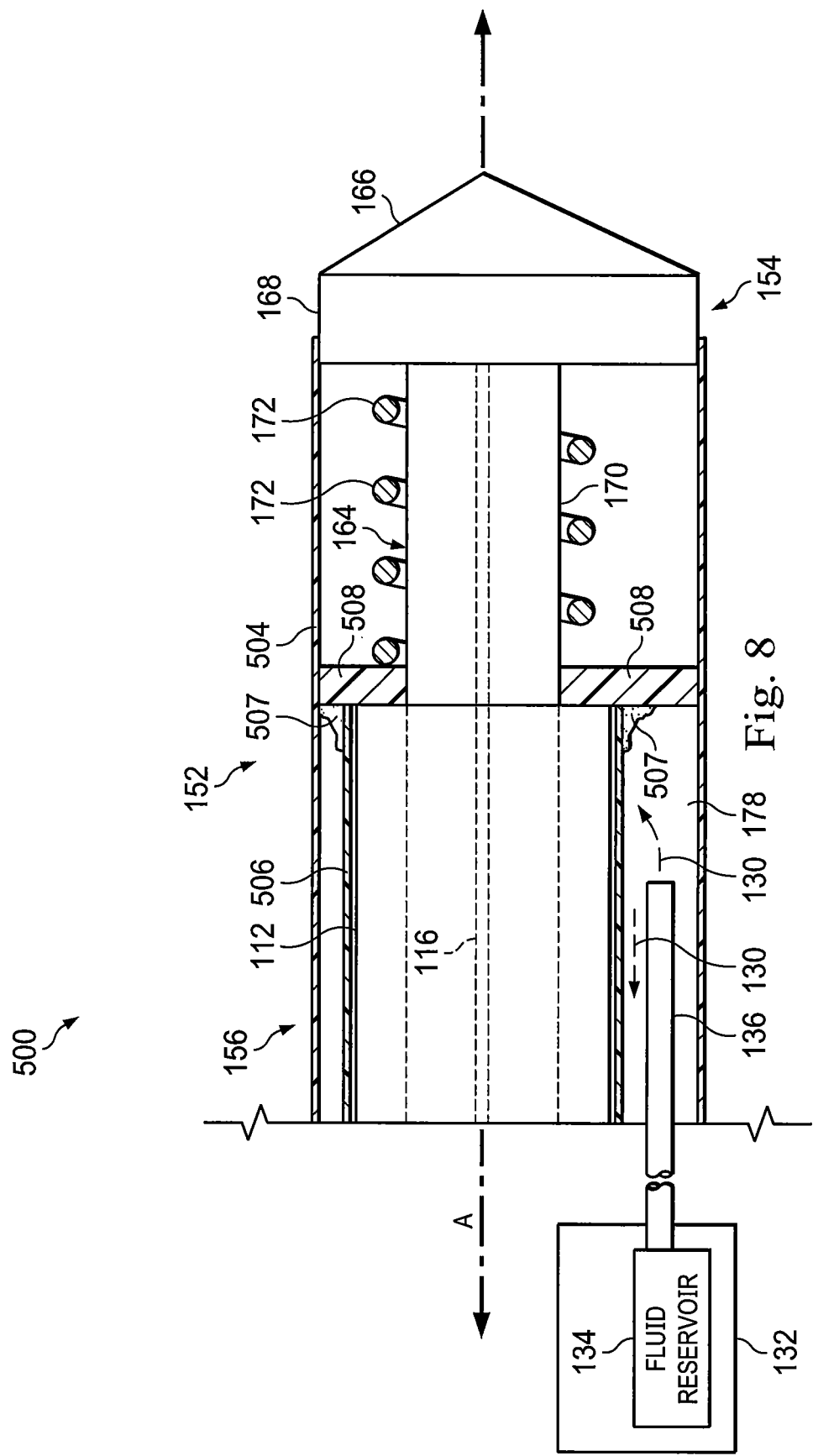
FIG. 8 is a cross-sectional end view of an energy delivery system with a plug preventing fluid migration.

FIG. 8 is a cross-sectional side view of an energy delivery system 500. Energy delivery system 500 may be substantially similar to energy delivery system 150 with the differences as described. In this embodiment, a ring-shaped plug 508 is positioned at a distal end of and co-axial with the outer conductor 112, around the insulator 164. In alternative embodiments, the plug 508 may be positioned more proximal, around the distal end portion of the outer conductor 112. The plug may be formed from a polymer material. An outer jacket 504 extends along the antenna instrument 102. In this embodiment, the outer jacket 504 is closed, sealed, or otherwise restricts fluid from passing into or out of the jacket. In alternative embodiments, a jacket may have openings, slits, or otherwise be unsealed along any portion of jacket to allow fluid to pass into the jacket or out from the jacket. The jacket may be formed from a thermoplastic or other flexible and fluid impermeable materials. A distal end portion of the jacket 504 is bonded to the insulator 164. The plug 508 is bonded to or otherwise abuts the jacket 504 to create a seal preventing migration of fluid 130 from the channel 178 into an area around the antenna 154. In this embodiment, fluid 130 delivered by the conduit 136 may be evacuated around the conduit 136, through the channel 178. A barrier layer 506 may surround the outer conductor 112 to prevent contact with the fluid 130. The barrier layer 506 may be sealed using, for example a glue or other adhesive material, to prevent fluid from migrating into contact with the outer conductor 112.

FIG. 9 illustrates a method 600 for transferring energy to an ablation target site according to some embodiments. The method 600 is illustrated as a set of operations or processes 602 through 608. Not all of the illustrated processes 602 through 608 may be performed in all embodiments of method 600. Additionally, one or more processes that are not expressly illustrated in FIG. 9 may be included before, after, in between, or as part of the processes 602 through 608. In some embodiments, one or more of the processes 602 through 608 may be implemented, at least in part, in the form of executable code stored on non-transitory, tangible, machine-readable media that when run by one or more processors (e.g., the processors of a control system) may cause the one or more processors to perform one or more of the processes. In one or more embodiments, the one or more of the processes may be performed by a control system (e.g., control system 712).

At a process 602, a cooling fluid, such as cooling fluid 130, may be received through a channel (e.g., channel 128, 178) to cool an antenna, such as dipole antenna 104, 154 or any of the previously described antennas. The cooling fluid may also be used to dissipate heat from the target tissue and/or the transmission member coupled to the antenna. As described above, the cooling fluid may be delivered by a fluid cooling system such as system 132. The process 602 may continue while all or some of the processes 604-608 are performed. At an optional process 604, the antenna may be positioned near a target site to perform an ablation. At a process 606, energy may be conducted through the transmission member (e.g., transmission member 106, 156) to the antenna. At a process 608, energy may be radiated from the antenna to ablate target patient tissue. In various embodiments, the temperature, delivery flow rate, and evacuation flow rate of the fluid may be controlled by operator selection or altered in a closed-loop fashion automatically under control of a computer processor based on sensor feedback during any of the processes 602-608.

FIG. 12 illustrates a method 900 for manufacturing an energy delivery system (e.g., similar to system 220 or others previously described). Not all of the illustrated processes of method 900 may be performed in all embodiments. Additionally, one or more processes that are not expressly illustrated in FIG. 12 may be included before, after, in between, or as part of the illustrated processes.

At a process 902, a jacket (e.g. jacket 224) may be connected to a tip section (e.g., tip section 222). At a process 904, an antenna instrument may be assembled by connecting the coil (e.g. coil 120) around the insulator (e.g., insulator 114) and connecting the coil to the elongate transmission member (e.g., elongate transmission member 106). In some embodiments, a barrier layer may also be extend over the antenna instrument. At a process 906, the antenna instrument may be inserted into the central lumen of the jacket and coupled to the tip section. Similarly, the cooling fluid conduit(s) (e.g. fluid conduit 136) may be inserted into the central lumen of the jacket. At a process 908, proximal end components including components of the fluid cooling system 132, handles, and/or connectors may be coupled to the proximal end of the antenna assembly.

FIG. 13 illustrates a method 950 for manufacturing an energy delivery system (e.g., similar to system 300 or others previously described). Not all of the illustrated processes of method 950 may be performed in all embodiments. Additionally, one or more processes that are not expressly illustrated in FIG. 13 may be included before, after, in between, or as part of the illustrated processes.

At a process 952, a jacket including multiple lumens or channels (e.g. channels 310, 302) may be coupled at a distal end to a single lumen jacket portion. The single lumen jacket portion may provide a transition area to allow fluid to flow from a delivery channel such as channel 302 into a return channel such as channel 310. At a process 954, an antenna instrument may be assembled by connecting the coil (e.g. coil 120) around the insulator (e.g., insulator 114) and connecting the coil to the elongate transmission member (e.g., elongate transmission member 106). In some embodiments, a barrier layer may also be extend over the antenna instrument. At a process 956, the antenna instrument may be inserted into the central lumen of the jacket assembly. The antenna instrument may be inserted from the proximal or distal end of the jacket assembly. At a process 958, the tip section may be coupled to the jacket assembly and the antenna instrument. At a process 960, proximal end components including components of the fluid cooling system 132, handles, and/or connectors may be coupled to the proximal end of the antenna assembly.

Figure 10:
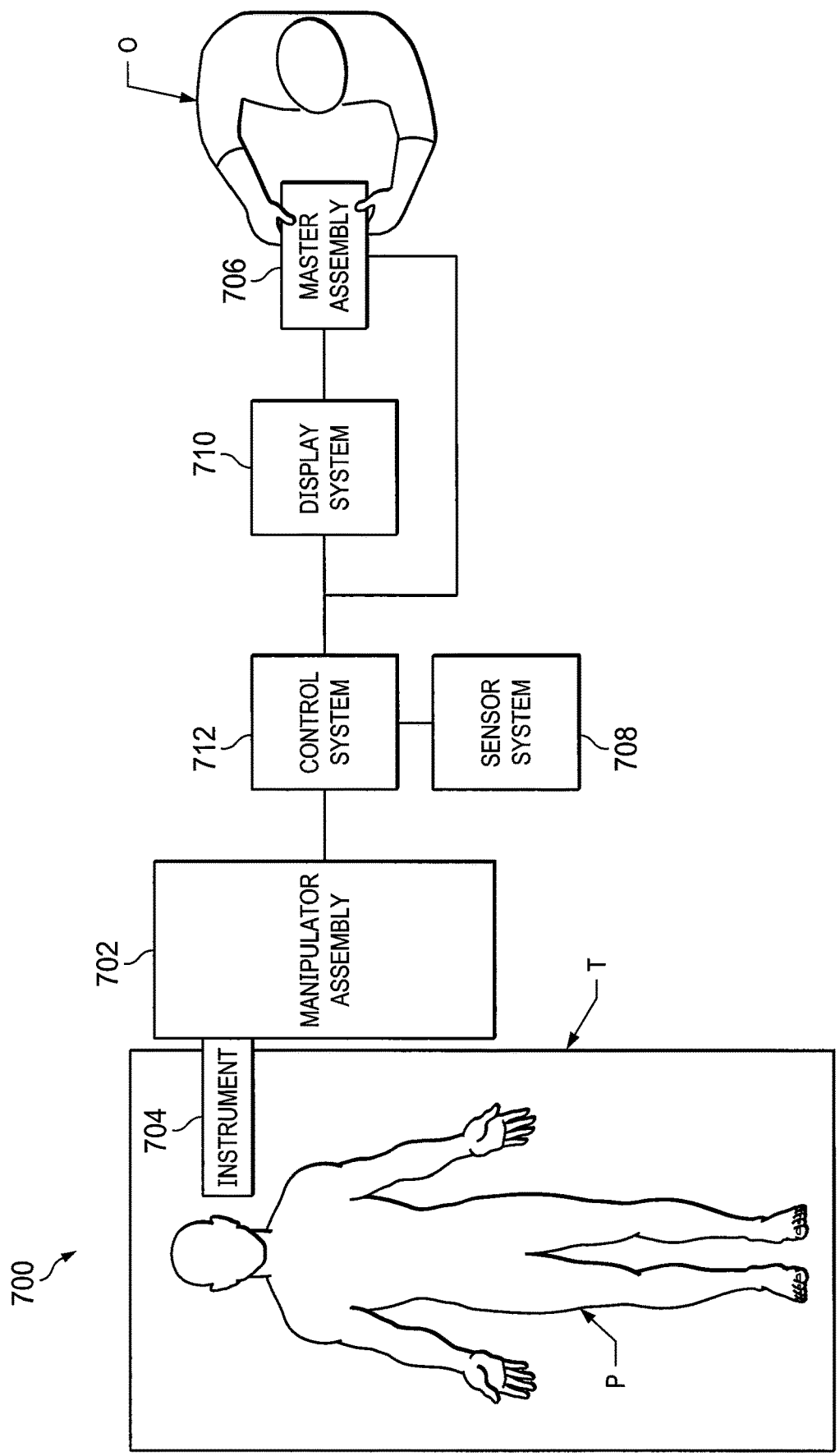
FIG. 10 is a simplified diagram of a teleoperated medical system according to some embodiments.

In various embodiments, any of the described energy delivery systems may be may be used as a medical instrument delivered by, coupled to, and/or controlled by a robotic teleoperated and/or non-teleoperated medical system. FIG. 10 is a simplified diagram of a teleoperated medical system 700 according to some embodiments. In some embodiments, teleoperated medical system 700 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 10, medical system 700 generally includes a manipulator assembly 702 for operating a medical instrument 704 in performing various procedures on a patient P positioned on a table T. In some embodiments, the medical instrument 704 may include, deliver, couple to, and/or control any of the antenna instruments described herein. The manipulator assembly 702 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Master assembly 706 generally includes one or more control devices for controlling manipulator assembly 702. Manipulator assembly 702 supports medical instrument 704 and may optionally include a plurality of actuators or motors that drive inputs on medical instrument 704 in response to commands from a control system 712. The actuators may optionally include drive systems that when coupled to medical instrument 704 may advance medical instrument 704 into a naturally or surgically created anatomic orifice. Other drive systems may move the distal end of medical instrument 704 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 704 for grasping tissue in the jaws of a biopsy device and/or the like. Actuator position sensors such as resolvers, encoders, potentiometers, and other mechanisms may provide sensor data to medical system 700 describing the rotation and orientation of the motor shafts. This position sensor data may be used to determine motion of the objects manipulated by the actuators.

Teleoperated medical system 700 also includes a display system 710 for displaying an image or representation of the surgical site and medical instrument 704 generated by subsystems of sensor system 708 and/or any auxiliary information related to a procedure including information related to ablation (e.g. temperature, impedance, energy delivery power levels, frequency, current, energy delivery duration, indicators of tissue ablation, etc.). Display system 710 and master assembly 706 may be oriented so operator O can control medical instrument 704 and master assembly 706 with the perception of telepresence.

In some embodiments, medical instrument 704 may include components of an imaging system, which may include an imaging scope assembly or imaging instrument that records a concurrent or real-time image of a surgical site and provides the image to the operator or operator O through one or more displays of medical system 700, such as one or more displays of display system 710. The concurrent image may be, for example, a two or three-dimensional image captured by an imaging instrument positioned within the surgical site. In some embodiments, the imaging system includes endoscopic imaging instrument components that may be integrally or removably coupled to medical instrument 704. However, in some embodiments, a separate endoscope, attached to a separate manipulator assembly may be used with medical instrument 704 to image the surgical site. In some embodiments, the imaging system includes a channel (not shown) that may provide for a delivery of instruments, devices, catheters, and/or the antenna instruments described herein. The imaging system may be implemented as hardware, firmware, software or a combination thereof which interact with or are otherwise executed by one or more computer processors, which may include the processors of the control system 712.

Teleoperated medical system 700 may also include control system 712. Control system 712 includes at least one memory and at least one computer processor (not shown) for effecting control between medical instrument 704, master assembly 706, sensor system 708, and display system 710. Control system 712 also includes programmed instructions (e.g., a non-transitory machine-readable medium storing the instructions) to implement some or all of the methods described in accordance with aspects disclosed herein, including instructions for providing information to display system 710.

Control system 712 may optionally further include a virtual visualization system to provide navigation assistance to operator O when controlling medical instrument 704 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

FIG. 11A is a simplified diagram of a medical instrument system 800 according to some embodiments. Medical instrument system 800 includes elongate device 802, such as a flexible catheter, coupled to a drive unit 804. Elongate device 802 includes a flexible body 816 having proximal end 817 and distal end or tip portion 818. Medical instrument system 800 further includes a tracking system 830 for determining the position, orientation, speed, velocity, pose, and/or shape of distal end 818 and/or of one or more segments 824 along flexible body 816 using one or more sensors and/or imaging devices as described in further detail below.

Tracking system 830 may optionally track distal end 818 and/or one or more of the segments 824 using a shape sensor 822. Shape sensor 822 may optionally include an optical fiber aligned with flexible body 816 (e.g., provided within an interior channel (not shown) or mounted externally). The optical fiber of shape sensor 822 forms a fiber optic bend sensor for determining the shape of flexible body 816. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. In some embodiments, tracking system 830 may optionally and/or additionally track distal end 818 using a position sensor system 820. Position sensor system 820 may be a component of an EM sensor system with position sensor system 820 including one or more conductive coils that may be subjected to an externally generated electromagnetic field. In some embodiments, position sensor system 820 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, an optical fiber sensor may be used to measure temperature or force. In some embodiments, a temperature sensor, a force sensor, an impedance sensor, or other types of sensors may be included within the flexible body.

Flexible body 816 includes a channel 821 sized and shaped to receive a medical instrument 826. In various embodiments, any of the antenna instruments described above may be inserted through the channel 821 of the flexible body 816. FIG. 11B is a simplified diagram of flexible body 816 with medical instrument 826 extended according to some embodiments. In some embodiments, medical instrument 826 may be used for procedures such as imaging, visualization, surgery, biopsy, ablation, illumination, irrigation, or suction. Medical instrument 826 can be deployed through channel 821 of flexible body 816 and used at a target location within the anatomy. Medical instrument 826 may include, for example, image capture probes, biopsy instruments, laser ablation fibers, and/or other surgical, diagnostic, or therapeutic tools. Medical instrument 826 may be used with an imaging instrument (e.g., an image capture probe) also within flexible body 816. The imaging instrument may include a cable coupled to the camera for transmitting the captured image data. In some examples, the imaging instrument may be a fiber-optic bundle, such as a fiberscope, that couples to image processing system 831. The imaging instrument may be single or multi-spectral, for example capturing image data in one or more of the visible, infrared, and/or ultraviolet spectrums. Medical instrument 826 may be advanced from the opening of channel 821 to perform the procedure and then retracted back into the channel when the procedure is complete. Medical instrument 826 may be removed from proximal end 817 of flexible body 816 or from another optional instrument port (not shown) along flexible body 816.

Flexible body 816 may also house cables, linkages, or other steering controls (not shown) that extend between drive unit 804 and distal end 818 to controllably bend distal end 818 as shown, for example, by broken dashed line depictions 819 of distal end 818. In some examples, at least four cables are used to provide independent "up-down" steering to control a pitch of distal end 818 and "left-right" steering to control a yaw of distal end 818. Steerable elongate devices are described in detail in U.S. patent application Ser. No. 13/274,208 (filed Oct. 14, 2011) (disclosing "Catheter with Removable Vision Probe"), which is incorporated by reference herein in its entirety.

The information from tracking system 830 may be sent to a navigation system 832 where it is combined with information from image processing system 831 and/or the pre-operatively obtained models to provide the operator with real-time position information. In some examples, the real-time position information may be displayed on display system 710 of FIG. 10 for use in the control of medical instrument system 800. In some examples, control system 712 of FIG. 10 may utilize the position information as feedback for positioning medical instrument system 800. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 800 may be teleoperated within medical system 700 of FIG. 10. In some embodiments, manipulator assembly 706 of FIG. 10 may be replaced by direct operator control. In some examples, the direct operator control may include various handles and operator interfaces for hand-held operation of the instrument.

One or more elements in embodiments of this disclosure may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In one embodiment, the control system supports wireless communication protocols such as Bluetooth, IrDA, HomeRF, IEEE 802.11, DECT, and Wireless Telemetry.

Medical tools that may be delivered through the flexible elongate devices or catheters disclosed herein may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. Medical tools may include image capture probes that include a stereoscopic or monoscopic camera for capturing images (including video images). Medical tools may additionally house cables, linkages, or other actuation controls (not shown) that extend between its proximal and distal ends to controllably bend the distal end of antenna instrument 102. Steerable instruments are described in detail in U.S. Pat. No. 7,416,681 (filed on Oct. 4, 2005) (disclosing "Articulated Surgical Instrument for Performing Minimally Invasive Surgery with Enhanced Dexterity and Sensitivity") and U.S.

patent application Ser. No. 12/286,644 (filed Sep. 30, 2008) (disclosing "Passive Preload and Capstan Drive for Surgical Instruments"), which are incorporated by reference herein in their entireties.

The systems described herein may be suited for navigation and treatment of anatomic tissues, via natural or surgically created connected passageways, in any of a variety of anatomic systems, including the lung, colon, stomach, the intestines, the kidneys and kidney calices, bladder, liver, gall bladder, pancreas, spleen, the ureter, ovaries, uterus, the brain, the circulatory system including the heart, vasculature, and/or the like.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An energy delivery system comprising:
a transmission member;
an antenna at a distal end of the transmission member, the antenna including a first conductive arm, an insulator extending around the first conductive arm, and a second conductive arm, wherein the second conductive arm includes a coil;
a barrier layer radially spaced from the insulator and surrounding the transmission member and the antenna, wherein the barrier layer extends from a proximal portion of the transmission member to a distal portion of the antenna; and
a jacket surrounding the barrier layer and forming a fluid channel for flow of a cooling fluid.

2. The energy delivery system of claim 1 wherein the barrier layer extends continuously from the proximal portion of the transmission member to the distal portion of the antenna.

3. The energy delivery system of claim 1 wherein the barrier layer comprises a fluid-insulating material.

4. The energy delivery system of claim 1 wherein the barrier layer comprises a material for providing rigidity to support the antenna.

5. The energy delivery system of claim 1, wherein a distal portion of the jacket is coupled to the barrier layer.

6. The energy delivery system of claim 1, wherein the jacket is formed from a thermoplastic material.

7. The energy delivery system of claim 1, wherein a distal section of the insulator forms a pointed tip.

8. The energy delivery system of claim 1, further comprising a tip section positioned distally to the antenna, wherein the jacket is coupled to the tip section.

9. The energy delivery system of claim 1 further comprising:
a fluid cooling system for providing the cooling fluid to the fluid channel.

10. The energy delivery system of claim 1 further comprising:
a first conduit member extending within the fluid channel, wherein the cooling fluid is received through the first conduit member.

11. The energy delivery system of claim 10 further comprising:
a second conduit member extending within the fluid channel, wherein the cooling fluid moves through the first conduit member in a first direction and moves through the second conduit member in a second direction, opposite the first direction.

12. The energy delivery system of claim 1 wherein the fluid channel has a D-shape.

13. The energy delivery system of claim 1 wherein the jacket includes a balloon portion extending around the antenna.

14. The energy delivery system of claim 1, wherein the coil of the second conductive arm is wound tightly around the insulator such that an outer diameter of the coil is approximately the same as an outer diameter of the transmission member.

15. The energy delivery system of claim 1, further comprising a plug positioned between the transmission member and the second conductive arm.

16. The energy delivery system of claim 15, wherein the plug is positioned to prevent migration of the cooling fluid distally of the transmission member.

17. The energy delivery system of claim 1 further comprising a divider extending longitudinally within the fluid channel to separate a first sub-channel wherein the cooling fluid flows in a first direction from a second sub-channel wherein the cooling fluid flows in a second direction, opposite the first direction.

18. The energy delivery system of claim 17 wherein the divider is a tube surrounding the barrier layer, the tube extending within and concentric with the jacket such that the first sub-channel is concentric with the second sub-channel.

19. An energy delivery system comprising:
a transmission member;
an antenna at a distal end of the transmission member, the antenna including a first conductive arm, an insulator extending around the first conductive arm, and a second conductive arm, wherein the second conductive arm includes a coil;
a barrier layer surrounding the transmission member and the antenna, wherein the barrier layer extends from a proximal portion of the transmission member to a distal portion of the antenna;
a jacket surrounding the barrier layer and forming a fluid channel for flow of a cooling fluid; and
a divider extending longitudinally within the fluid channel to separate a first sub-channel in which the cooling fluid flows in a first direction from a second sub-channel in which the cooling fluid flows in a second direction opposite the first direction, wherein the divider is a tube surrounding the barrier layer, the tube extending within and concentric with the jacket such that the first sub-channel is concentric with the second sub-channel, and wherein the divider is coupled at a first longitudinal edge to the barrier layer and at a second longitudinal edge to the jacket.

20. An energy delivery system comprising:
- a transmission member;
- an antenna at a distal end of the transmission member, the antenna including a first conductive arm, an insulator extending around the first conductive arm, and a second conductive arm, wherein the second conductive arm includes a coil and a distal section of the insulator forms a pointed tip;
- a barrier layer surrounding the transmission member and the antenna, wherein the barrier layer extends from a proximal portion of the transmission member to a distal portion of the antenna;
- a jacket surrounding the barrier layer and forming a fluid channel for flow of a cooling fluid; and
- a ring extending around the insulator, wherein the ring is positioned proximal to the pointed tip and wherein a distal portion of the jacket is coupled to the ring.

* * * * *